United States Patent
Bulinski et al.

(10) Patent No.: US 11,325,893 B2
(45) Date of Patent: May 10, 2022

(54) HYDROFLUOROETHERS AND METHODS OF USING SAME

(71) Applicants: 3M INNOVATIVE PROPERTIES COMPANY, St. Paul, MN (US); Matthew Toso

(72) Inventors: Michael J. Bulinski, Stillwater, MN (US); William M. Lamanna, Stillwater, MN (US); Forrest A. Coughlin, Chaska, MN (US); Hui Ren, Woodbury, MN (US); Nicholas A. Toso, Minneapolis, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 17/278,418

(22) PCT Filed: Sep. 23, 2019

(86) PCT No.: PCT/IB2019/058037
§ 371 (c)(1),
(2) Date: Mar. 22, 2021

(87) PCT Pub. No.: WO2020/065492
PCT Pub. Date: Apr. 2, 2020

(65) Prior Publication Data
US 2021/0395213 A1  Dec. 23, 2021

Related U.S. Application Data

(60) Provisional application No. 62/736,681, filed on Sep. 26, 2018.

(51) Int. Cl.
C09K 5/04 (2006.01)
C07D 307/18 (2006.01)

(52) U.S. Cl.
CPC ............. *C07D 307/18* (2013.01); *C09K 5/04* (2013.01)

(58) Field of Classification Search
CPC ....... C07D 307/24; C07D 307/18; C09K 5/04
See application file for complete search history.

(56) References Cited

U.S. PATENT DOCUMENTS

| | | | |
|---|---|---|---|
| 8,261,560 B2 | 9/2012 | Flynn | |
| 8,791,254 B2 | 7/2014 | Viteak | |
| 2010/0139274 A1 | 6/2010 | Zyhowski | |
| 2015/0157596 A1* | 6/2015 | Brosnan | A61D 7/04 514/451 |

FOREIGN PATENT DOCUMENTS

JP  2010-047523  3/2010

OTHER PUBLICATIONS

Gervits, "Reaction of perfluoro-2-methyl-2-pentene and perfluoroisobutylene with a-oxides in the presence of cesium fluoride", 1981, vol. 30, No. 5, pp. 846-852.
Ellis, "Cleaning and Contamination of Electronics Components and Assemblies", Electrochemical Publications Limited, 1986, pp. 182-194.
International Search report for PCT International Application No. PCT/IB2019/058037 dated Dec. 20, 2019, 3 pages.

* cited by examiner

*Primary Examiner* — John R Hardee
(74) *Attorney, Agent, or Firm* — Jeffrey M. Olofson

(57) ABSTRACT

A compound is represented by the following general formula (I): (I) wherein each of Rf1 and Rf2 is, independently, F, CF3, C2F5, C3F7, or C4F9, with the proviso that if either of Rf1 and Rf2 is fluorine, then the other is not fluorine; Rf3 is F, CF3, C2F5, C3F7 or CF(CF3)2; Rf4 is F, CF3, C2F5, C3F7 or CF(CF3)2; and Rh is CH3 or C2H5.

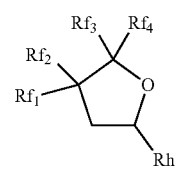

21 Claims, No Drawings

HYDROFLUOROETHERS AND METHODS OF USING SAME

CROSS REFERENCE TO RELATED APPLICATIONS

This application is a national stage filing under 35 U.S.C. 371 of PCT/IB2019/058037, filed Sep. 23, 2019, which claims the benefit of U.S. Provisional Application No. 62/736681, filed Sep. 26, 2018, the disclosure of which is incorporated by reference in its/their entirety herein.

FIELD

The present disclosure relates to hydrofluoroethers, uses for, and methods of making the same.

BACKGROUND

Various hydrofluoroethers compounds are described in, for example, U.S. Pat. No. 8,791,254 and U.S. Pat. App. Pub. 2005/0127322.

SUMMARY

In some embodiments, an HFE compound is provided. The HFE compound is represented by the following general formula (I):

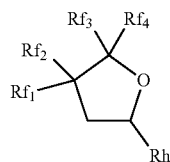

wherein each of $Rf_1$ and $Rf_2$ is, independently, F, $CF_3$, $C_2F_5$, $C_3F_7$, or $C_4F_9$, with the proviso that if either of $Rf_1$ and $Rf_2$ is fluorine, then the other is not fluorine;
$Rf_3$ is F, $CF_3$, $C_2F_5$, $C_3F_7$ or $CF(CF_3)_2$;
$Rf_4$ is F, $CF_3$, $C_2F_5$, $C_3F_7$ or $CF(CF_3)_2$; and
$Rh$ is $CH_3$ or $C_2H_5$.

In some embodiments, an apparatus for heat transfer is provided. The apparatus includes a device; and a mechanism for transferring heat to or from the device. The mechanism comprises a heat transfer fluid that comprises a compound represented by general formula (I):

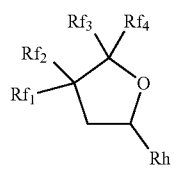

where each of $Rf_1$ and $Rf_2$ is, independently, F, $CF_3$, $C_2F_5$, $C_3F_7$, or $C_4F_9$ with the proviso that if either of $Rf_1$ and $Rf_2$ is fluorine, then the other is not fluorine;
$Rf_3$ is F, $CF_3$, $C_2F_5$, $C_3F_7$ or $CF(CF_3)_2$;
$Rf_4$ is F, $CF_3$, $C_2F_5$, $C_3F_7$ or $CF(CF_3)_2$; and
$Rh$ is $CH_3$, $C_2H_5$, or H.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

In view of an increasing demand for environmentally friendly and low toxicity chemical compounds for use as working fluids, it is recognized that there exists an ongoing need for new working fluids that can meet the performance requirements (e.g., nonflammability, solvency, stability, operating temperature range) of a variety of different applications (e.g., heat transfer, solvent cleaning, deposition coating solvents), and be manufactured cost-effectively, all while exhibiting desirable environmental profiles (e.g., low toxicity, low global warming potential).

Generally, the present disclosure provides a new class of fluorinated compounds useful as working fluids. The new fluorinated compounds are cyclic hydrofluoroethers (HFEs), which provide many of the beneficial physical properties of similar HFEs but, surprisingly, exhibit significantly higher boiling points and significantly lower atmospheric lifetimes and global warming potentials.

As used herein, "fluoro-" (for example, in reference to a group or moiety, such as in the case of "fluoroalkylene" or "fluoroalkyl" or "fluorocarbon") or "fluorinated" means (i) partially fluorinated such that there is at least one carbon-bonded hydrogen atom, or (ii) perfluorinated.

As used herein, "perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure is directed to hydrofluoroether compounds represented by the following general formula (I):

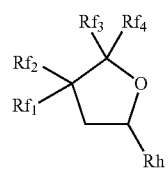

(I)

where each of $Rf_1$ and $Rf_2$ is, independently, F, $CF_3$, $C_2F_5$, $C_3F_7$, or $C_4F_9$ with the proviso that if either of $Rf_1$ and $Rf_2$ is fluorine, then the other is not fluorine; $Rf_3$ is F, $CF_3$, $C_2F_5$, $C_3F_7$ or $CF(CF_3)_2$; $Rf_4$ is F, $CF_3$, $C_2F_5$, $C_3F_7$ or $CF(CF_3)_2$; and Rh is $CH_3$, $C_2H_5$ or H. In some embodiments, $Rf_1$ and $Rf_2$ are either both $CF_3$ or $Rf_1$ is $CF_3$ and $Rf_2$ is $C_2F_5$ or $C_3F_7$ or $C_4F_9$. In some embodiments, $Rf_3$ is $C_2F_5$ or $CF(CF_3)_2$. In some embodiment, Rh is H or $CH_3$.

In some embodiments, again with reference to the hydrofluoroether compounds represented by general formula (I), each of $Rf_1$ and $Rf_2$ is, independently, F, $CF_3$, $C_2F_5$, $C_3F_7$, or $C_4F_9$, with the proviso that if either of $Rf_1$ and $Rf_2$ is fluorine, then the other is not fluorine; $Rf_3$ is F, $CF_3$, $C_2F_5$, $C_3F_7$ or $CF(CF_3)2$; $Rf_4$ is F, $CF_3$, $C_2F_5$, $C_3F_7$ or $CF(CF_3)_2$; and Rh is $CH_3$, or $C_2H_5$. In some embodiments, $Rf_1$ and $Rf_2$ are either both $CF_3$ or $Rf_1$ is $CF_3$ and $Rf_2$ is $C_2F_5$ or $C_3F_7$ or $C_4F_9$. In some embodiments, $Rf_3$ is $C_2F_5$ or $CF(CF_3)_2$. In some embodiments, Rh is $CH_3$.

In some embodiments, still with reference to the hydrofluoroether compounds represented by general formula (I), $Rf_1$ is $CF_3$, $C_2F_5$ or $C_3F_7$; $Rf_2$ is $C_2F_5$, $C_3F_7$, or $C_4F_9$; $Rf_3$ is $CF(CF_3)_2$ or $C_3F_7$; $Rf_4$ is F; and Rh is H. In some embodiments, $Rf_1$ is $CF_3$ and $Rf_2$ is $C_2F_5$, $C_3F_7$ or $C_4F_9$. In some embodiments, $Rf_3$ is $C_2F_5$ or $CF(CF_3)_2$.

In some embodiments, again with reference to the hydrofluoroether compounds represented by general formula (I), one or two pairs of perfluoroalkyl groups (Rf) from among $Rf_1$, $Rf_2$, $Rf_3$, and $Rf_4$ (e.g., $Rf_1$ and $Rf_4$ or $Rf_2$ and $Rf_3$) may be linked together to form a 5 or 6 membered perfluorinated carbon ring. Any of $Rf_1$, $Rf_2$, $Rf_3$, and $Rf_4$ that are not linked together may have any of the above described definitions.

In some embodiments, still with reference to the hydrofluoroether compounds represented by general formula (I), $Rf_1$ and $Rf_4$ and/or $Rf_2$ and $Rf_3$ may be linked together to form a 5 or 6 membered perfluorinated- carbon ring. Alternatively, $Rf_1$ and $Rf_2$ and/or $Rf_3$ and $Rf_4$ may be linked together to form a 5 or 6 membered perfluorinated carbon ring.

Any of $Rf_1$, $Rf_2$, $Rf_3$, and $Rf_4$ that are not linked together may have any of the above described definitions.

In any of the above described embodiments, no more than one of the Rf groups ($Rf_1$-$Rf_4$), no more than two of the Rf groups ($Rf_1$-$Rf_4$), or no more than three of the Rf groups ($Rf_1$-$Rf_4$) is a F atom.

It is to be appreciated that for purposes of the present disclosure, empirical formulas of the type $C_nF_{2n+1}$ refer to any and all isomers of that substituent group.

In various embodiments, representative examples of the compounds of general formula (I) include the following:

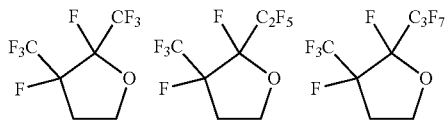

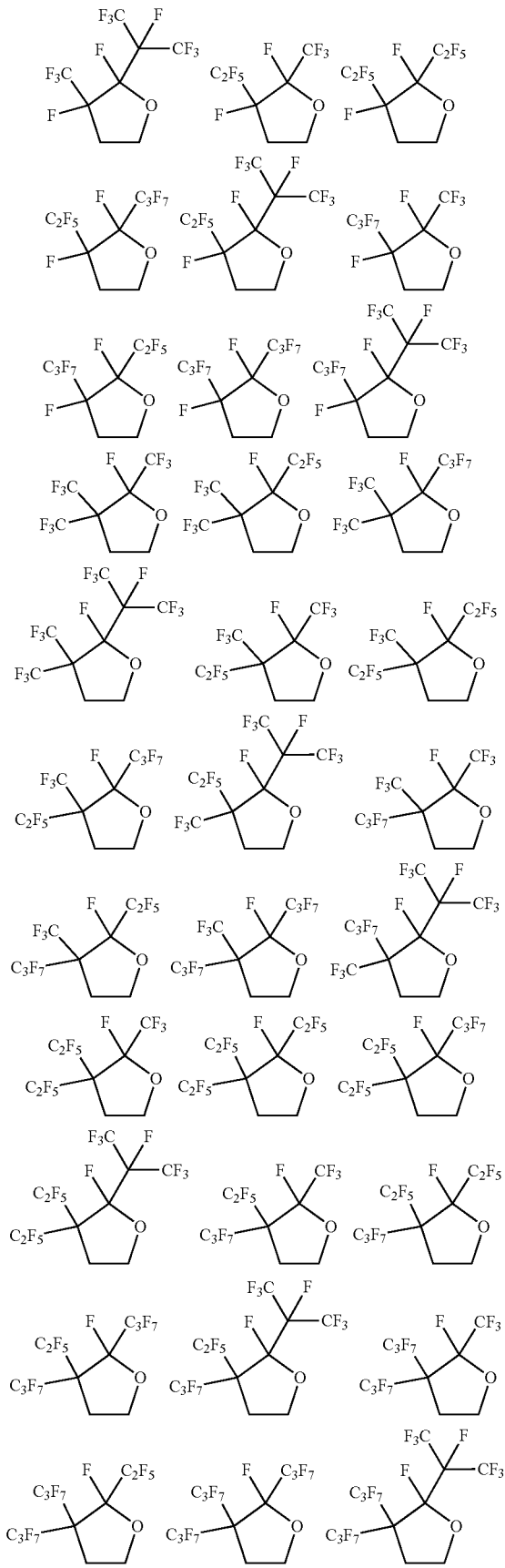

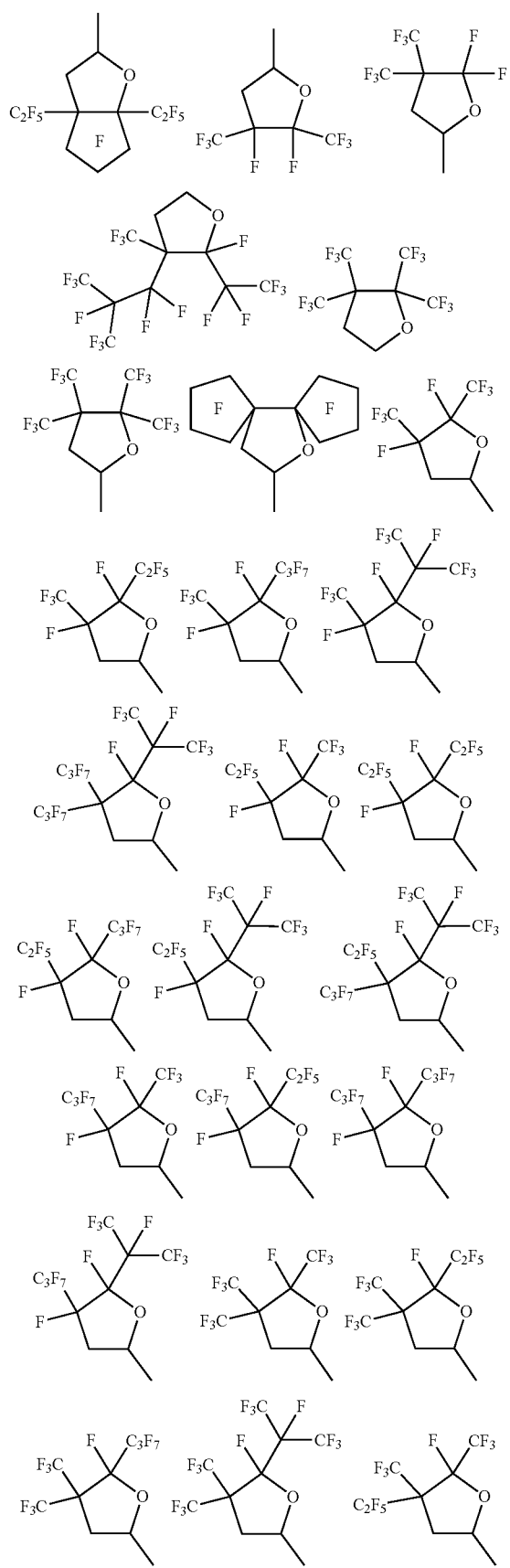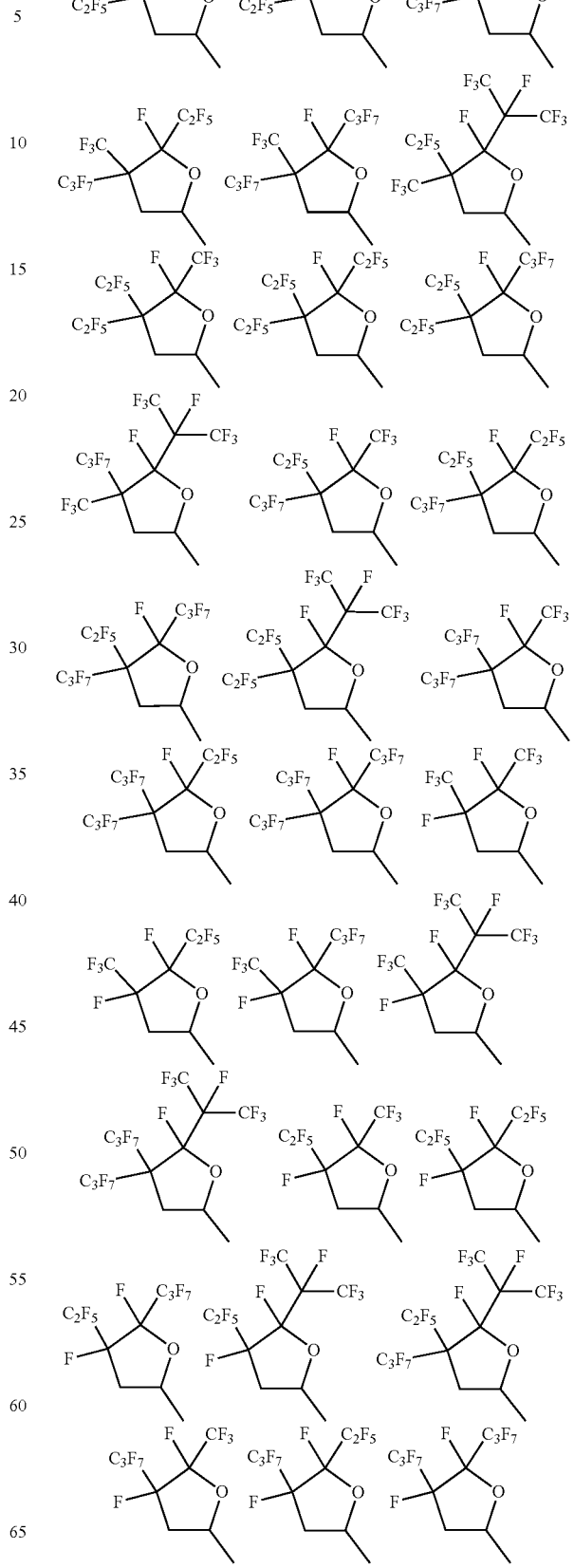

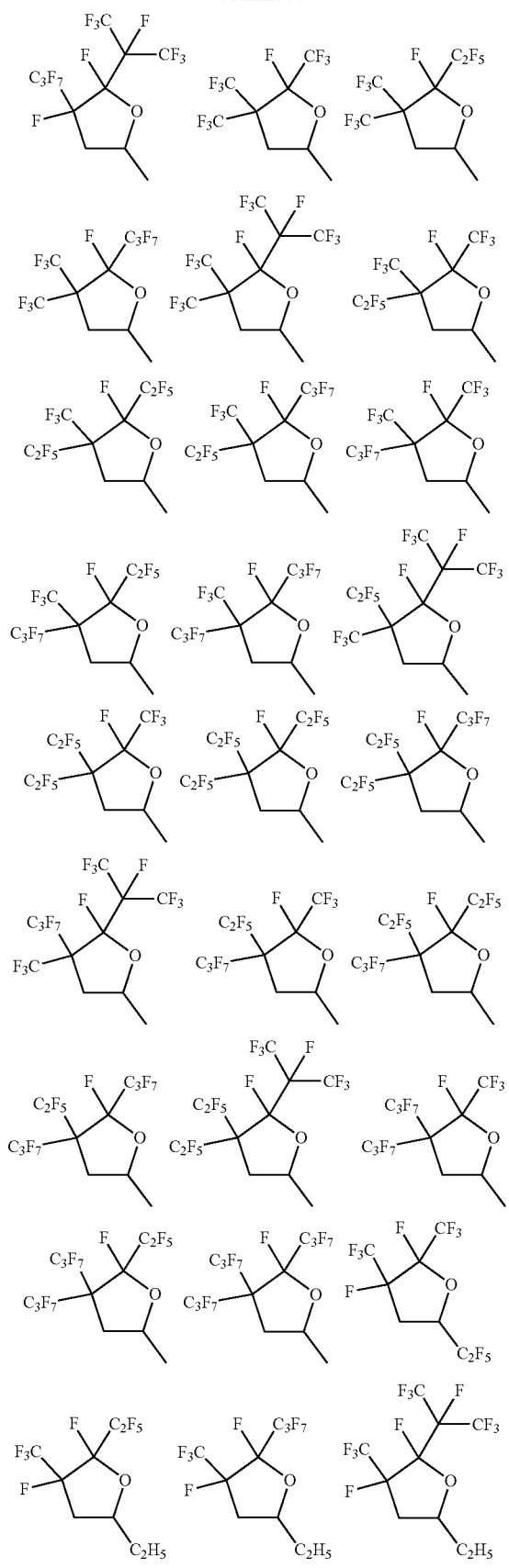
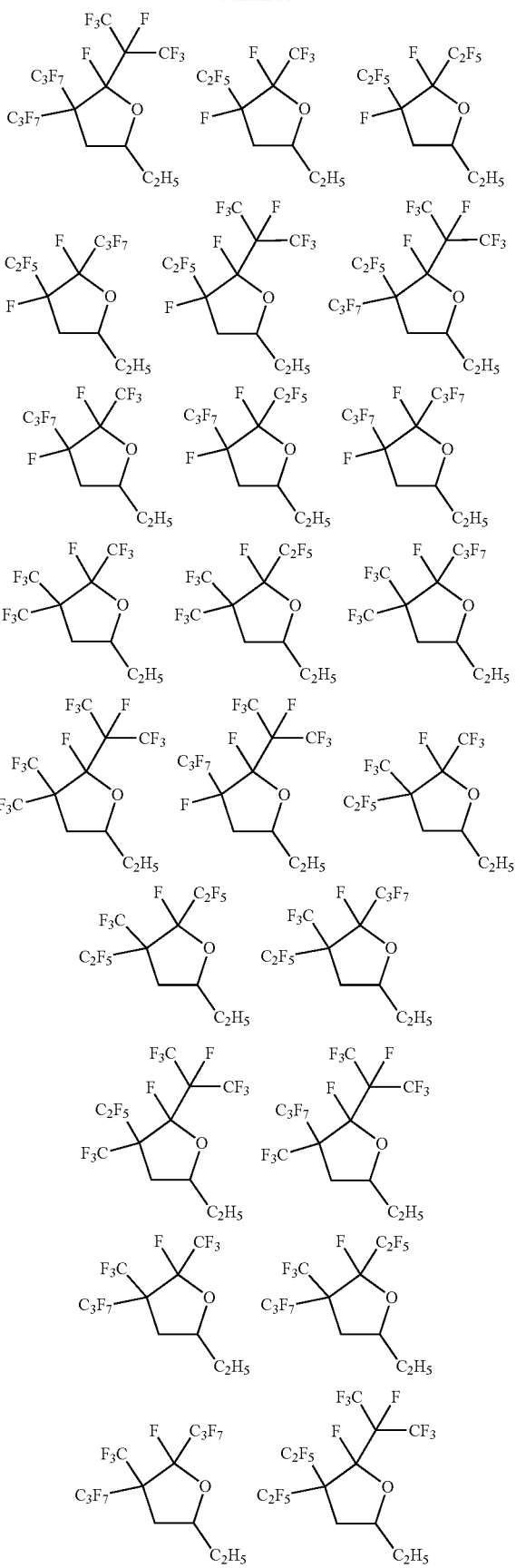

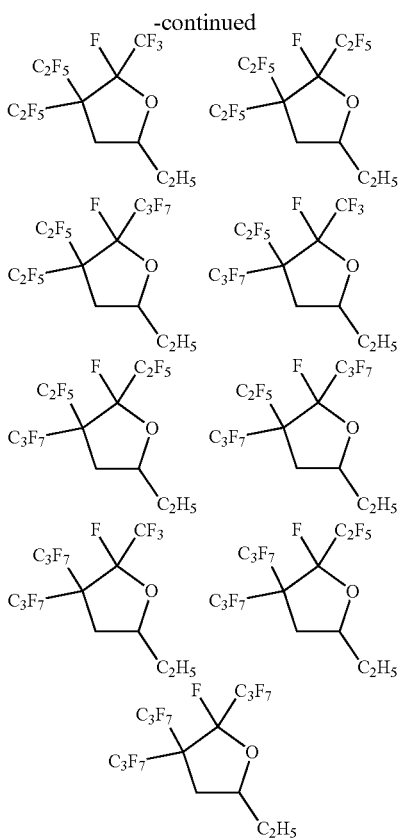

In some embodiments, the cyclic HFE compounds of the present disclosure may be hydrophobic, relatively chemically unreactive, and thermally stable. The cyclic HFE compounds may have a low environmental impact. In this regard, the cyclic HFE compounds of the present disclosure may have a global warming potential (GWP) of less than 500, 300, 200, 100, 20 or less than 10. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i [C(t)] dt}{\int_0^{ITH} a_{CO_2} [C_{CO_2}(t)] dt} = \frac{\int_0^{ITH} a_i C_{oi} e^{-t/\tau_i} dt}{\int_0^{ITH} a_{CO_2} [C_{CO_2}(t)] dt}$$

In this equation a, is the radiative forcing per unit mass increase of a compound in the atmosphere (the change in the flux of radiation through the atmosphere due to the IR absorbance of that compound), C is the atmospheric concentration of a compound, τ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In some embodiments, the cyclic HFE compounds represented by general formula (I) can be synthesized using reactants such as 2-chloroethanol, 2-bromoethanol, 1-bromo-2-propanol, 1-chloro-2-propanol, 2-bromo-1-butanol, 2-chloro-1-butanol, ethylene oxide, propylene oxide, ethylene carbonate, propylene carbonate and reacting said reactants with a perfluorinated olefin as described in general formula (II):

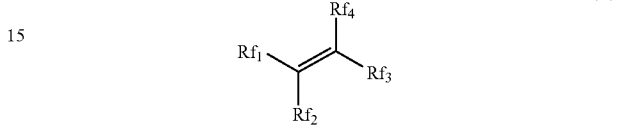
(II)

where each of $Rf_1$ and $Rf_2$ is, independently, F, $CF_3$, $C_2F_5$, $C_3F_7$, or $C_4F_9$, with the proviso that if either of $Rf_1$ and $Rf_2$ is F, then the other is not fluorine; and $Rf_3$ is F, $CF_3$, $C_2F_5$, $C_3F_7$, or $CF(CF_3)_2$; and $Rf_4$ is F, $CF_3$, $C_2F_5$, $C_3F_7$ or $CF(CF_3)_2$.

In some embodiments, no more than one of the Rf groups, or no more than two of the Rf groups, or no more than three of the Rf groups in general formula (II) is a F atom.

In some embodiments, one or two pairs of perfluoroalkyl groups (Rf) in general formula (II) may be linked together to form a 5 or 6 membered perfluorinated carbon ring. Thus $Rf_1$ and $Rf_2$ may be linked together and/or $Rf_3$ and $Rf_4$ may be linked together to form a perfluorinated ring structure. Alternatively, $Rf_1$ and $Rf_4$ may be linked together and/or $Rf_2$ and $Rf_3$ may be linked together to form a perfluorinated ring structure.

In some embodiments, the cyclic HFE compounds of general formula (I) can be synthesized by reacting a perfluorinated olefin of general Formula (II) with a vicinal haloalcohol, such as those vicinal haloalcohols listed above, in the presence of at least a stoichiometric of base, as described in JP 2010047523.

Alternatively, in some embodiments, the cyclic HFE compounds represented by general formula (I) can be synthesized by reacting a perfluorinated olefin of general Formula (II) with a cyclic organic carbonate in the presence of a catalyst. Suitable cyclic organic carbonates include, but are not limited to, ethylene carbonate, propylene carbonate, or butylene carbonate. In various embodiments, the cyclic organic carbonate is ethylene carbonate or propylene carbonate. Suitable catalysts include various salts of nucleophilic anions, including halide and pseudo halide anions. In certain embodiments the catalyst is a halide salt, such as a chloride, bromide, or iodide salt. Optionally, additional co-catalysts or phase transfer catalysts, such as crown ethers, quaternary ammonium salts, and other aprotic onium salts may be employed to further increase the rate of reaction.

In yet further embodiments, the cyclic HFE compounds represented by general formula (I) can be synthesized by reacting a perfluorinated olefin of general Formula (II) with an organic epoxide in the presence of a catalyst, such as the catalysts described above. Suitable organic epoxides include, for example, ethylene oxide, propylene oxide, or butylene oxide. In various embodiments, the organic epoxide is ethylene oxide or propylene oxide.

The catalytic processes of the present disclosure in which cyclic organic carbonate or organic epoxide reactants are employed provide significant advantages in terms of cost, atom efficiency, as well as safety in some cases. In this regard, cyclic organic carbonates are generally low cost and relatively safe (e.g., low toxicity) reactants relative to most vicinal haloalcohols. Additionally, the only waste byproduct formed from the reaction with the cyclic organic carbonates is $CO_2$ gas. Regarding organic epoxides, such reactants are also generally low-cost reactants compared to most vicinal haloalcohols and no waste byproducts are formed from the reaction, thus achieving 100% atom efficiency.

In some embodiments, the above-discussed syntheses can be carried out in an aprotic organic solvent or in the absence of solvent. Suitable aprotic organic solvents include, for example, diglyme, tetraglyme, dimethylformamide (DMF), acetonitrile, N-methylpyrolidinone (NMP), sulfolane, dimethylsulfoxide, and adiponitrile. Alternatively, excess cyclic organic carbonate or excess organic epoxide can serve as the solvent as well as reactant.

In some embodiments, the perfluorinated olefin of general formula (II) may be generated catalytically in situ from an isomeric perfluorinated olefin through a catalytic isomerization reaction and subsequently reacted with a cyclic organic carbonate or an organic epoxide to synthesize the cyclic HFE of general Formula (I). The isomerization of the initial perfluorinated olefin may be conducted using the same catalyst(s) used to catalyze the reaction of the perfluorinated olefin of general Formula (II) with the cyclic organic carbonate or organic epoxide, or a different catalyst may be used. In this way, both the isomerization of the initial perfluorinated olefin to form the perfluoroolefin isomer of general formula (II) and the reaction of the perfluorinated olefin of general formula (II) with a cyclic organic carbonate or an organic epoxide to form the cyclic HFE of general formula (I) can be carried out in a single pot. A specific example of such a one-pot synthesis is illustrated in Scheme (I), where EC is ethylene carbonate and EO is ethylene oxide.

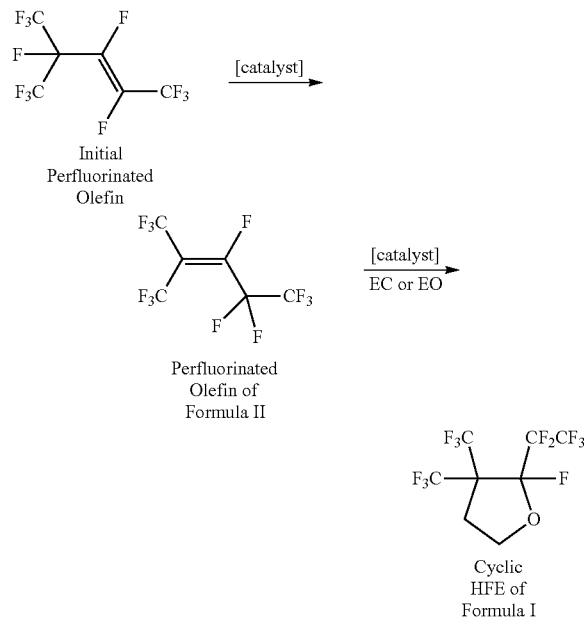

Scheme (I)

In some embodiments, the present disclosure is further directed to working fluids that include the above-described cyclic HFE compounds as a major component. For example, the working fluids may include at least 25%, at least 50%, at least 70%, at least 80%, at least 90%, at least 95%, or at least 99% by weight of the above-described cyclic HFE compounds based on the total weight of the working fluid. In addition to the cyclic HFE compounds, the working fluids may include a total of up to 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, fluorinated nitriles, perfluorinated nitriles, perfluorosulfones, hydrochlorocarbons, hydrochlorofluorocarbons, hydrofluorocarbons, hydrofluoroolefins, hydrochloroolefins, hydrochlorofluoroolefins, hydrofluoroethers, perfluoroketones, or mixtures thereof, based on the total weight of the working fluid. Such additional components can be chosen to modify or enhance the properties of a composition for a particular use.

In some embodiments, the present disclosure is further directed to an apparatus for heat transfer that includes a device and a mechanism for transferring heat to or from the device. The mechanism for transferring heat may include a heat transfer working fluid that includes a cyclic HFE compound of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, heat exchangers, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner.

The provided apparatus may include a mechanism for transferring heat. The mechanism may include a heat transfer fluid. The heat transfer fluid may include one or more cyclic HFE compounds of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

In some embodiments, the present disclosure is directed to an apparatus for converting thermal energy into mechanical energy in a Rankine cycle. The apparatus may include a working fluid that includes one or more cyclic HFE compounds of the present disclosure. The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

In some embodiments, the present disclosure relates to a process for converting thermal energy into mechanical energy in a Rankine cycle. The process may include using a heat source to vaporize a working fluid that includes one or more cyclic HFE compounds of the present disclosure to form a vaporized working fluid. In some embodiments, the heat is transferred from the heat source to the working fluid in an evaporator or boiler.

The vaporized working fluid may pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. In order to prevent methane gas from entering the environment and thus contributing to global warming, the methane gas generated by the landfills can be burned by way of "flares" producing carbon dioxide and water which are both less harmful to the environment in terms of global warming potential than methane. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may expand though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

The desired thermodynamic characteristics of organic Rankine cycle working fluids are well known to those of ordinary skill and are discussed, for example, in U.S. Pat. Appl. Publ. No. 2010/0139274 (Zyhowski et al.). The greater the difference between the temperature of the heat source and the temperature of the condensed liquid or a provided heat sink after condensation, the higher the Rankine cycle thermodynamic efficiency. The thermodynamic efficiency is influenced by matching the working fluid to the heat source temperature. The closer the evaporating temperature of the working fluid to the source temperature, the higher the efficiency of the system. Toluene can be used, for example, in the temperature range of 79° C. to about 260° C., however toluene has toxicological and flammability concerns. Fluids such as 1,1-dichloro-2,2,2-trifluoroethane and 1,1,1,3,3-pentafluoropropane can be used in this temperature range as an alternative. But 1,1-dichloro-2,2,2-trifluoroethane can form toxic compounds below 300° C. and need to be limited to an evaporating temperature of about 93° C. to about 121° C. Thus, there is a desire for other environmentally-friendly Rankine cycle working fluids with higher critical temperatures so that source temperatures such as gas turbine and internal combustion engine exhaust can be better matched to the working fluid.

In some embodiments, the present disclosure relates to coating compositions that include a solvent composition that one or more cyclic HFE compounds of the present disclosure, and one or more coating materials which are soluble or dispersible in the solvent composition.

In various embodiments, the coating materials of the coating compositions may include pigments, lubricants, stabilizers, adhesives, anti-oxidants, dyes, polymers, pharmaceuticals, release agents, inorganic oxides, and the like, and combinations thereof. For example, coating materials may include perfluoropolyether, hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, perfluoropolyethers, polysiloxanes, stearic acid, acrylic adhesives, polytetrafluoroethylene, amorphous copolymers of tetrafluoroethylene, or combinations thereof.

In some embodiments, the above-described coating compositions can be useful in coating deposition, where the cyclic HFE compounds function as a carrier for a coating material to enable deposition of the material on the surface of a substrate. In this regard, the present disclosure further relates to a process for depositing a coating on a substrate surface using the coating composition. The process comprises the step of applying to at least a portion of at least one surface of a substrate a coating of a liquid coating composition comprising (a) a solvent composition containing one or more of the cyclic HFE compounds; and (b) one or more coating materials which are soluble or dispersible in the solvent composition. The solvent composition can further comprise one or more co-dispersants or co-solvents and/or one or more additives (e.g., surfactants, coloring agents, stabilizers, anti-oxidants, flame retardants, and the like). Preferably, the process further comprises the step of removing the solvent composition from the coating by, e.g., allowing evaporation (which can be aided by the application of, e.g., heat or vacuum).

In various embodiments, to form a coating composition, the components of the coating composition (i.e., the cyclic HFE compound(s), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating. For example, the coating material(s) may constitute from about 0.1 to about 10 weight percent of the coating composition.

In illustrative embodiments, the deposition process of the disclosure can be carried out by applying the coating composition to a substrate by any conventional technique. For example, the composition can be brushed or sprayed (e.g., as an aerosol) onto the substrate, or the substrate can be spin-coated. In some embodiments, the substrate may be coated by immersion in the composition. Immersion can be carried out at any suitable temperature and can be maintained for any convenient length of time. If the substrate is a tubing, such as a catheter, and it is desired to ensure that the composition coats the lumen wall, the composition may be drawn into the lumen by the application of reduced pressure.

In various embodiments, after a coating is applied to a substrate, the solvent composition can be removed from the coating (e.g., by evaporation). If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Both organic and inorganic substrates can be coated by the processes of the present disclosure. Representative examples of the substrates include metals, ceramics, glass, polycarbonate, polystyrene, acrylonitrile-butadiene-styrene copolymer, natural fibers (and fabrics derived therefrom) such as cotton, silk, fur, suede, leather, linen, and wool, synthetic fibers (and fabrics) such as polyester, rayon, acrylics, nylon, or blends thereof, fabrics including a blend of natural and synthetic fibers, and composites of the foregoing materials. In some embodiments, substrates that may be coated include, for example, magnetic hard disks or electrical connectors with perfluoropolyether lubricants or medical devices with silicone lubricants.

In some embodiments, the present disclosure relates to cleaning compositions that include one or more cyclic HFE compounds of the present disclosure, and one or more co-solvents. In some embodiments, the cyclic HFE compounds may be present in an amount greater than 50 weight percent, greater than 60 weight percent, greater than 70 weight percent, or greater than 80 weight percent based upon the total weight of the cyclic HFE compounds and the co-solvent(s).

In various embodiments, the cleaning composition may further comprise a surfactant. Suitable surfactants include those surfactants that are sufficiently soluble in the fluorinated olefin, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylatedalkyl phenols, ethoxylated fatty acids, alkylarysulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble oil removal. The surfactant, if used, can be added in an amount sufficient to promote soil removal. Typically, surfactant is added in amounts from about 0.1 to 5.0 wt. %, preferably in amounts from about 0.2 to 2.0 wt. % of the cleaning composition.

In illustrative embodiments, the co-solvent may include alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, cyclic HFEs, hydrochloroolefins, hydrochlorofluoroolefins, hydrofluoroethers, perfluorosulfones, perfluoronitriles or mixtures thereof. Representative examples of co-solvents which can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof.

In some embodiments, the present disclosure relates to a process for cleaning a substrate. The cleaning process can be carried out by contacting a contaminated substrate with a cleaning composition as discussed above. The cyclic HFE compounds can be utilized alone or in admixture with each other or with other commonly-used cleaning solvents, e.g., alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, cyclic HFEs, hydrochloroolefins, hydrochlorofluoroolefins, hydrofluoroethers, perfluorosulfones, perfluoronitriles or mixtures thereof. Such co-solvents can be chosen to modify or enhance the solvency properties of a cleaning composition for a particular use and can be utilized in ratios (of co-solvent to cyclic HFE compounds) such that the resulting composition has no flash point. If desirable for a particular application, the cleaning composition can further contain one or more dissolved or dispersed gaseous, liquid, or solid additives (for example, carbon dioxide gas, surfactants, stabilizers, antioxidants, or activated carbon).

In some embodiments, the present disclosure relates to cleaning compositions that include one or more cyclic HFE compounds of the present disclosure and optionally one or more surfactants. Suitable surfactants include those surfactants that are sufficiently soluble in the cyclic HFE compounds, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylated alkylphenols, ethoxylated fatty acids, alkylaryl sulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble soil removal. The surfactant, if used, can be added in an amount sufficient to promote soil removal. Typically, surfactant may be added in amounts from 0.1 to 5.0 wt. % or from 0.2 to 2.0 wt. % of the cleaning composition.

The cleaning processes of the disclosure can also be used to dissolve or remove most contaminants from the surface of a substrate. For example, materials such as light hydrocarbon contaminants; higher molecular weight hydrocarbon contaminants such as mineral oils and greases; fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes; particulates; water; and other contaminants encountered in precision, electronic, metal, and medical device cleaning can be removed.

The cleaning compositions can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies,* Electrochemical Publications Limited, Ayr, Scotland, pages 182-94 (1986).

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

For decades, PFC fluids have been used in specialty, usually high value electronic cooling applications and were often placed in direct contact with the electronics being cooled. Examples include military electronics and supercomputer applications. PFC fluids were favored because they are very inert and excellent dielectrics. More recently HFCs, HFEs, and PFKs have been examined for these applications.

More mainstream electronics like servers and desktop computers have historically used air cooling, but recently the demand for more computing power has caused chip powers to rise to the level that liquid cooling has begun to emerge in high performance machines, due to improved efficiency. Aqueous working fluids are preferred from a performance standpoint in indirect contact liquid phase systems, but raise reliability concerns due to their propensity to cause short circuits if a leak should develop. Dielectric liquids should be nonflammable for similar reasons, since a fire could break out in the event of a leak. A dielectric liquid's environmental properties must also be consistent with the environmental requirements of the computer manufacturer and its customers. PFC liquids (including perfluorinated hydrocarbon, perfluorinated amine and perfluorinated ether and polyether liquids) and HFC liquids are not ideal candidates for this application due to their high GWPs, thus there is a continuing need to develop materials that can provide improved environmental profiles, while also satisfying all the other requirements for direct contact electronic immersion cooling.

The HFEs of the present disclosure generally meet the performance and environmental requirements for this application. Their safety, nonflammability, high dielectric strength, low volume resistivity, material compatibility, and excellent heat transfer properties are suitable for direct contact cooling and use with highly valuable electronics with excellent reliability. In addition, their short atmospheric lifetime translates to significantly reduced GWP and minimal impact as greenhouse gases.

For example, modern power semiconductors like Field Effect Transistors (FETs) and Insulated Gate Bipolar Transistors (IGBTs) generate very high heat fluxes. These devices are used in the power converter modules in hybrid electric vehicles. These devices must function under conditions of extreme heat and cold and this has spurred the adoption of direct contact cooling technologies. The liquids used in these applications must again be electrically insulating, non-flammable, compatible with the electronic components they are in contact with, and provide a level of environmental sustainability consistent with the environmental goals of the hybrid technology. The HFEs of the present disclosure generally meet these requirements.

The cyclic HFEs of the present disclosure, alone or in combination, may be employed as fluids for transferring heat from various electronic components by direct contact to provide thermal management and maintain optimal component performance under extreme operation conditions. Illustrative materials are cyclic HFEs with boiling points from about 100° C. to about 150° C. (in some embodiments from about 120° C. to about 150° C., about 160° C. to about 190° C., or even about 195° C. to about 250° C.).

Direct contact fluid immersion technology is well known to be useful for thermal management of electronic components. Hydrofluoroethers and perfluoroketones are two examples of environmentally sustainable chemistries that have been used for many years in direct contact fluid immersion heat transfer applications that place stringent performance requirements on the fluids employed, such as non-flammability, low toxicity, small environmental footprint (zero ODP, low GWP), high dielectric strength, low dielectric constant, high volume resistivity, stability, and good thermal properties. These fluids have found use in many thermal management applications that include semiconductor manufacturing, and electronics cooling (e.g. power electronics, transformers, computers/servers, batteries and battery packs). Surprisingly, it has been discovered that the cyclic HFEs of the present disclosure generally provide higher than expected boiling points as well as lower than expected GWPs compared to non-cyclic segregated HFEs. The cyclic HFEs of the disclosure also provide improved hydrolytic stability compared to perfluoroketones and non-cyclic segregated HFEs. Thus, cyclic HFEs of the present disclosure have recently been found to provide a unique balance of properties that makes them highly attractive fluid candidates for use in direct contact immersion cooling applications.

In some embodiments, the present disclosure describes the use of HFEs as single-phase immersion cooling fluids for electronics. Single phase immersion cooling has a long history in computer server cooling. There is no phase change in single phase immersion. Instead the liquid warms and cools as it flows or is pumped through the computer hardware and a heat exchanger, respectively, thereby transferring heat away from the server. The fluids used in single phase immersion cooling of servers must meet the same requirements as outlined above while also having a boiling point exceeding about 75 degrees C. to limit evaporative losses. The HFEs of the present disclosure generally meet these requirements.

In some embodiments, the present disclosure may be directed to an immersion cooling system which operates by single-phase immersion cooling. Generally, the single phase immersion cooling system may include a heat generating component disposed within the interior space of a housing such that it is at least partially immersed (and up to fully immersed) in the liquid phase of the working fluid. The single-phase system may further include a pump and a heat exchanger, the pump operating to move the working fluid to and from the heat generating components and the heat exchanger operating to cool the working fluid. The heat exchanger may be disposed within or external to the housing.

In some embodiments, the present disclosure is directed to a thermal management system of a battery pack (e.g., a lithium ion battery pack) A thermal management system for a lithium-ion battery pack includes a lithium-ion battery pack, and any of the above-described HFEs or working fluid in thermal communication with the lithium-ion battery pack.

In some embodiments, the present disclosure may be directed to methods for cooling electronic components. Generally, the methods may include at least partially immersing a heat electronic generating component (e.g., a computer server) in a liquid that includes the above-described HFEs or working fluid. The method may further include transferring heat from the heat generating electronic component using the above-described HFE or working fluid.

Listing of Embodiments

1. A compound represented by the following general formula (I):

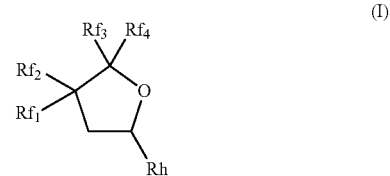

wherein each of $Rf_1$ and $Rf_2$ is, independently, F, $CF_3$, $C_2F_5$, $C_3F_7$, or $C_4F_9$, with the proviso that if either of $Rf_1$ and $Rf_2$ is fluorine, then the other is not fluorine;
$Rf_3$ is F, $CF_3$, $C_2F_5$, $C_3F_7$ or $CF(CF_3)_2$;
$Rf_4$ is F, $CF_3$, $C_2F_5$, $C_3F_7$ or $CF(CF_3)_2$; and
Rh is $CH_3$, or $C_2H_5$.

2. The compound of embodiment 1, wherein $Rf_1$ and $Rf_2$ are either both $CF_3$ or $Rf_1$ is $CF_3$ and $Rf_2$ is $C_2F_5$ or $C_3F_7$ or $C_4F_9$.

3. The compound according to any one of the previous embodiments, wherein $Rf_3$ is $C_2F_5$ or $CF(CF_3)_2$.

4. The compound according to any one of the previous embodiments, wherein Rh is $CH_3$.

5. A compound represented by the following general formula (I):

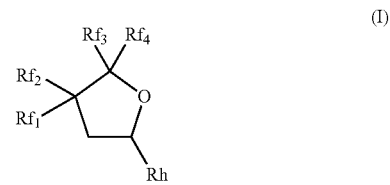

where $Rf_1$ is $CF_3$, $C_2F_5$ or $C_3F_7$;
$Rf_2$ is $C_2F_5$, $C_3F_7$, or $C_4F_9$;
$Rf_3$ is $CF(CF_3)_2$ or $C_3F_7$;
$Rf_4$ is F; and
Rh is H.

6. The compound of embodiment 5, wherein $Rf_1$ is $CF_3$ and $Rf_2$ is $C_2F_5$, $C_3F_7$ or $C_4F_9$.

7. A compound represented by the following general formula (I):

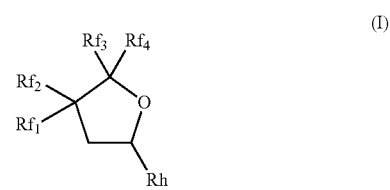

where one or two pairs of Rf groups from among $Rf_1$, $Rf_2$, $Rf_3$, and $Rf_4$ may be linked together to form a 5 or 6 membered perfluorinated carbon ring; and
Rh is $CH_3$, $C_2H_5$ or H;
wherein any of $Rf_1$, $Rf_2$, $Rf_3$, and $Rf_4$ that are not linked together are as follows:
each of $Rf_1$ and $Rf_2$ is, independently, F, $CF_3$, $C_2F_5$, $C_3F_7$, or $C_4F_9$ with the proviso that if either of $Rf_1$ and $Rf_2$ is fluorine, then the other is not fluorine;

$Rf_3$ is F, $CF_3$, $C_2F_5$, $C_3F_7$ or $CF(CF_3)_2$; and $Rf_4$ is F, $CF_3$, $C_2F_5$, $C_3F_7$ or $CF(CF_3)_2$.

8. A working fluid comprising the compound of any of the previous embodiments, wherein the compound is present in the working fluid at an amount of at least 25% by weight based on the total weight of the working fluid.

9. An apparatus for heat transfer comprising:
a device; and
a mechanism for transferring heat to or from the device, the mechanism comprising a working fluid that comprises a compound represented by the following general formula (I):

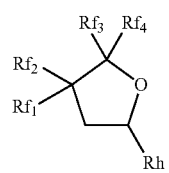

where each of $Rf_1$ and $Rf_2$ is, independently, F, $CF_3$, $C_2F_5$, $C_3F_7$, or $C_4F_9$ with the proviso that if either of $Rf_1$ and $Rf_2$ is fluorine, then the other is not fluorine;

$Rf_3$ is F, $CF_3$, $C_2F_5$, $C_3F_7$ or $CF(CF_3)_2$;

$Rf_4$ is F, $CF_3$, $C_2F_5$, $C_3F_7$ or $CF(CF_3)_2$; and

Rh is $CH_3$, $C_2H_5$ or H.

10. The apparatus for heat transfer of embodiment 9, wherein $Rf_1$ and $Rf_2$ are either both $CF_3$ or $Rf_1$ is $CF_3$ and $Rf_2$ is $C_2F_5$ or $C_3F_7$ or $C_4F_9$.

11. The apparatus for heat transfer of any one of embodiments 9-10, wherein $Rf_3$ is $C_2F_5$ or $CF(CF_3)_2$.

12. The apparatus for heat transfer of any one of embodiments 9-11, wherein Rh is H or $CH_3$.

13. The apparatus for heat transfer of embodiment 9, wherein the compound comprises the compound of any one of embodiments 1-7.

14. The apparatus for heat transfer of any one of embodiments 9-13, wherein the device is selected from a microprocessor, a semiconductor wafer used to manufacture a semiconductor device, a power control semiconductor, an electrochemical cell, a battery pack, an electrical distribution switch gear, a power transformer, a circuit board, a multichip module, a packaged or unpackaged semiconductor device, a fuel cell, and a laser.

15. The apparatus for heat transfer of any one of embodiments 9-14, wherein the mechanism for transferring heat is a component in a system for maintaining a temperature or temperature range of an electronic device.

16. A method of transferring heat comprising:
providing a device; and
transferring heat to or from the device using a heat transfer fluid that comprises a compound represented by the following general formula (I):

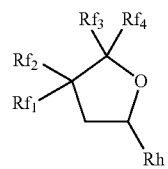

where each of $Rf_1$ and $Rf_2$ is, independently, F, $CF_3$, $C_2F_5$, $C_3F_7$, or $C_4F_9$ with the proviso that if either of $Rf_1$ and $Rf_2$ is fluorine, then the other is not fluorine;

$Rf_3$ is F, $CF_3$, $C_2F_5$, $C_3F_7$ or $CF(CF_3)_2$;

$Rf_4$ is F, $CF_3$, $C_2F_5$, $C_3F_7$ or $CF(CF_3)_2$; and

Rh is $CH_3$, $C_2H_5$ or H.

17. A process for making a compound having the following general formula (I):

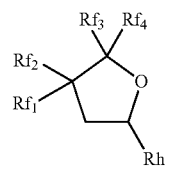

where each of $Rf_1$ and $Rf_2$ is, independently, F, $CF_3$, $C_2F_5$, $C_3F_7$, or $C_4F_9$ with the proviso that if either of $Rf_1$ and $Rf_2$ is fluorine, then the other is not fluorine;

$Rf_3$ is F, $CF_3$, $C_2F_5$, $C_3F_7$ or $CF(CF_3)_2$;

$Rf_4$ is F, $CF_3$, $C_2F_5$, $C_3F_7$ or $CF(CF_3)_2$; and Rh is $CH_3$, $C_2H_5$ or H, the process comprising the step of reacting a perfluorinated olefin having the following general structure (II)

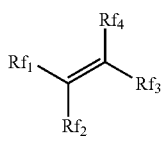

where each of $Rf_1$ and $Rf_2$ is, independently, F, $CF_3$, $C_2F_5$, $C_3F_7$, or $C_4F_9$, with the proviso that if either of $Rf_1$ and $Rf_2$ is F, then the other is not fluorine; and $Rf_3$ is F, $CF_3$, $C_2F_5$, $C_3F_7$, or $CF(CF_3)_2$; and $Rf_4$ is F, $CF_3$, $C_2F_5$, $C_3F_7$ or $CF(CF_3)_2$;

with a cyclic organic carbonate or an organic epoxide in the presence of a catalyst.

18. A process according to embodiment 17, wherein the cyclic organic carbonate comprises ethylene carbonate or propylene carbonate.

19. A process according to embodiment 17, wherein the organic epoxide comprises ethylene oxide or propylene oxide.

20. A process according to any one of embodiments 17-19, wherein the catalyst is a halide salt.

21. A process according to any one of embodiments 17-20, wherein the perfluorinated olefin of general structure (II) is generated in-situ from an isomeric perfluorinated olefin via catalytic isomerization.

22. A compound represented by the following general formula (I):

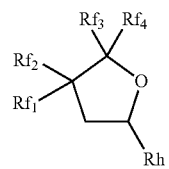

where each of $Rf_1$ and $Rf_2$ is, independently, F, $CF_3$, $C_2F_5$, $C_3F_7$, or $C_4F_9$ with the proviso that if either of $Rf_1$ and $Rf_2$ is fluorine, then the other is not fluorine;

$Rf_3$ is F, $CF_3$, $C_2F_5$, $C_3F_7$ or $CF(CF_3)_2$;

$Rf_4$ is F, $CF_3$, $C_2F_5$, $C_3F_7$ or $CF(CF_3)_2$; and

Rh is $CH_3$, $C_2H_5$ or H.

23. An apparatus for converting thermal energy into mechanical energy in a Rankine cycle comprising:

a working fluid;

a heat source to vaporize the working fluid and form a vaporized working fluid;

a turbine through which the vaporized working fluid is passed thereby converting thermal energy into mechanical energy;

a condenser to cool the vaporized working fluid after it is passed through the turbine; and a pump to recirculate the working fluid, wherein the working fluid comprises the compound according to any one of embodiments 1-7, 23, or the working fluid of embodiment 8.

24. A process for converting thermal energy into mechanical energy in a Rankine cycle comprising:

vaporizing a working fluid with a heat source to form a vaporized working fluid;

expanding the vaporized working fluid through a turbine;

cooling the vaporized working fluid using a cooling source to form a condensed working fluid; and pumping the condensed working fluid;

wherein the working fluid comprises the compound according to any one of embodiments 1-7, 23, or the working fluid of embodiment 8.

25. A process for recovering waste heat comprising:

passing a liquid working fluid through a heat exchanger in communication with a process that produces waste heat to produce a vaporized working fluid;

removing the vaporized working fluid from the heat exchanger;

passing the vaporized working fluid through an expander, wherein the waste heat is converted into mechanical energy; and cooling the vaporized working fluid after it has been passed through the expander;

wherein the working fluid comprises the compound according to any one of embodiments 1-7, 23, or the working fluid of embodiment 8.

26. A coating composition comprising:

a solvent composition comprising a compound or working fluid according to any one of embodiments 1-8 and 23; and a coating material that is soluble or dispersible in said solvent composition.

27. The coating composition of embodiment 26, wherein said coating material comprises a pigment, lubricant, stabilizer, adhesive, anti-oxidant, dye, polymer, pharmaceutical, release agent, inorganic oxide.

28. The composition according of embodiment 26, wherein said coating material comprises a perfluoropolyether, a hydrocarbon, a silicone lubricant, a copolymer of tetrafluoroethylene, or a polytetrafluoroethylene.

29. A cleaning composition comprising:

a compound or working fluid according to any one of embodiments 1-8 and 23; and a co-solvent.

30. The cleaning composition of embodiment 29, wherein said compound or working fluid is greater than 50 percent by weight of said composition based on the total weights of the compound and the co-solvent.

31. The cleaning composition according to any one of embodiments 29-30, wherein said co-solvent comprises alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, cyclic HFEs, hydrochloroolefins, hydrochlorofluoroolefins, hydrofluoroethers, perfluoronitriles, perfluorosulfones, or mixtures thereof.

32. A cleaning composition comprising:

a compound or working fluid according to any one of embodiments 1-8 and 23; and a surfactant.

33. The cleaning composition of embodiment 33, wherein the cleaning composition comprises from 0.1 to 5 percent by weight of the surfactant.

34. The cleaning composition according to any one of embodiments 32-33, wherein the surfactant comprises a nonionic surfactant comprising an ethoxylated alcohol, an ethoxylated alkylphenol, an ethoxylated fatty acid, an alkylaryl sulfonate, a glycerolester, an ethoxylated fluoroalcohol, a fluorinated sulfonamide, or mixtures thereof 35. A process for removing contaminants from a substrate, the process comprising the steps of:

contacting a substrate with a composition comprising:

a compound or working fluid according to any one of embodiments 1-8 and 23; and a co-solvent.

35. An immersion cooling system comprising:

a housing having an interior space;

a heat-generating component disposed within the interior space; and a working fluid liquid disposed within the interior space such that the heat-generating component is in contact with the working fluid liquid;

wherein the working fluid comprises the compound according to any one of embodiments 1-7, 23, or the working fluid of embodiment 8.

36. The immersion cooling system of embodiment 35, wherein the compound is present in the working fluid at an amount of at least 25% by weight based on the total weight of the working fluid.

37. The immersion cooling system of any one of embodiments 35-36, wherein the heat-generating component comprises an electronic device.

38. The immersion cooling system of any one of embodiments 35-37, wherein the electronic device comprises a computer server.

39. The immersion cooling system of embodiment 38, wherein the computer server operates at a frequency of less than 3 GHz.

40. The immersion cooling system of any one of embodiments 35-39, wherein the immersion cooling system further comprises a heat exchanger disposed within the system such that the heated liquid working fluid contacts the heat exchanger;

41. The immersion cooling system of any one of embodiments 35-40, wherein the immersion cooling system comprises a single-phase immersion cooling system.

42. The immersion cooling system of any one of embodiments 35-41, wherein the immersion cooling system further comprises a pump that is configured to move the working fluid to and from a heat exchanger.

43. A thermal management system comprising:
   a battery pack; and
   a working fluid disposed within the thermal management system such that the working fluid is in thermal communication with the battery pack;
   wherein the working fluid comprises the compound according to any one of embodiments 1-7, 23, or the working fluid of embodiment 8.

44. A method for cooling a heat generating component, the method comprising:
   at least partially immersing a heat generating component in a working fluid; and
   transferring heat from the heat generating component using the working fluid;
   wherein the working fluid comprises the compound according to any one of embodiments 1-7, 23, or the working fluid of embodiment 8.

The operation of the present disclosure will be further described with regard to the following detailed examples. These examples are offered to further illustrate various embodiments and techniques. It should be understood, however, that many variations and modifications may be made while remaining within the scope of the present disclosure.

EXAMPLES

Objects and advantages of this disclosure are further illustrated by the following comparative and illustrative examples. Unless otherwise noted, all parts, percentages, ratios, etc. in the examples and the rest of the specification are by weight, and all reagents used in the examples were obtained, or are available, from general chemical suppliers such as, for example, Sigma-Aldrich Corp., Saint Louis, Mo., US or may be synthesized by conventional methods.

The following abbreviations are used in this section: mL=milliliter, h=hours, yr=years, g=grams, mol=moles, mmol=millimole, ° C.=degrees Celsius, amu=atomic mass units, pounds per square inch=psi, pounds per square inch gauge=psig, ppmv=parts per million by volume.

Sample Preparation Procedures

TABLE 1

Summary of Illustrative and Comparative Examples

| | Structure | Description | Source |
|---|---|---|---|
| Ex. 1 | (structure) | 2-fluoro-2-(1,1,2,2,2-pentafluoroethyl)-3,3-bis(trifluoromethyl)tetrahydrofuran | Preparation Procedures Provided Below |
| Ex. 2 | (structure) | 2-fluoro-3-(1,1,2,2,3,3,3-heptafluoropropyl)-2-[1,2,2,2-tetrafluoro-1-(trifluoromethyl)ethyl]-3-(trifluoromethyl)tetrahydrofuran | Preparation Procedures Provided Below |
| Ex. 3 | (structure) | 2-fluoro-5-methyl-2-(1,1,2,2,2-pentafluoroethyl)-3,3-bis(trifluoromethyl)tetrahydrofuran | Preparation Procedures Provided Below |
| Ex. 4 | (structure) | 2-fluoro-3-(1,1,2,2,3,3,3-heptafluoropropyl)-5-methyl-2-[1,2,2,2-tetrafluoro-1-(trifluoromethyl)ethyl]-3-(trifluoromethyl)tetrahydrofuran | Preparation Procedures Ptovided Below |
| Ex. 5 | (structure) | 5-methyl-2,2,3,3-tetrakis(trifluoromethyl)tetrahydrofuran | Preparation Procedures Provided Below |
| CE1 | (structure) | NOVEC 7300 | 3M Company, St. Paul, MN, US |
| CE2 | (structure) | NOVEC 7700 | 3M Company, St. Paul, MN, US |

Example 1: 2-fluoro-2-(1,1,2,2,2-pentafluoroethyl)-3,3-bis(trifluoromethyl)tetrahydrofuran Synthesis Procedure A for Example 1: In a 2L 3-neck round bottom flask equipped with magnetic stirring, thermocouple, cold water condenser, dry $N_2$ bubbler and a heating mantle, acetonitrile (802 g, 19535.9 mmol), trimethylamine (155.24g, 1534.1 mmol) and 2-bromoethanol (176.35 g, 1397.1 mmol) were combined. The 1,1,1,3,4,4,5,5,5-nonafluoro-2-(trifluoromethyl)pent-2-ene (417.08 g, 1390.1 mmol) was added via an addition funnel slowly to minimize the exotherm. When about two thirds of 1,1,1,3,4,4,5,5,5-nonafluoro-2-(trifluoromethyl)pent-2-ene had been added, white salts formed in the reaction mixture. When the addition was complete, the mixture was stirred at a temperature of 40° C. overnight. The reaction material was filtered to remove the majority of the salts, then was washed with DI water four times, a total of 375 g product was collected which was dried over molecular sieves and then filtered. The product was analyzed by GC-FID which indicated the reaction conversion of at least 74% to the product. The product was fractionally distilled (b.p.=150.1° C.). The product structure, as shown in Table 1, was confirmed by GC-MS and $^1H$, $^{19}F$ NMR.

Synthesis Procedure B for Example 1: Into a 300 mL Hastelloy Parr reactor were charged 12.2 g (0.0375 mol) tetrabutylammonium bromide catalyst, 90.4 g (1.027 mol) ethylene carbonate, and 70.8 g (0.236 mol) 1,1,1,3,4,4,5,5,5-nonafluoro-2-(trifluoromethyl)pent-2-ene. The reactor was immediately sealed and heated to 100° C. with stirring for a period of 3 hours during which time the pressure rose to a final pressure of 208 psi (due to $CO_2$ evolution). The reactor was then allowed to cool to room temperature overnight and residual pressure was vented. Once at atmospheric pressure, the reactor was disassembled and the reaction mixture was quenched with 200 mL water with stirring resulting in a two-phase liquid mixture. The lower fluorochemical phase was recovered and washed with two 150 mL portions of water in a separatory funnel to remove residual ethylene carbonate and bromide catalyst. After the final water washing, 65.10 g of crude fluorochemical product was recovered. The crude product was analyzed by GC-FID revealing that it consisted of 69.0% desired product (2-fluoro-2-(1,1,2,2,2-pentafluoroethyl)-3,3-bis(trifluoromethyl)tetrahydrofuran) and 13.6% unreacted 1,1,1,3,4,4,5,5,5-nonafluoro-2-(trifluoromethyl)pent-2-ene. The identity of the desired product was verified by GC-MS analysis which indicated a mass of 344 amu.

Synthesis Procedure C for Example 1: Into a 300 mL Hastelloy Parr reactor were charged 11.99 g (0.0372mol) tetrabutylammonium bromide catalyst, 90.3 g (1.027 mol) ethylene carbonate, and 71.50 g (0.238 mol) 1,1,1,2,3,4,5,5,5-nonafluoro-4-(trifluoromethyl)pent-2-ene. The reactor was immediately sealed and heated to 70° C. with stirring for a period of 4 days during which time the pressure rose to a final pressure of 132 psi (due to $CO_2$ evolution). Head space samples were taken from the reaction mixture at intervals during the 4 day hold and analyzed by GC-FID, indicating that isomerization of 1,1,1,2,3,4,5,5,5-nonafluoro-4-(trifluoromethyl)pent-2-ene to 1,1,1,3,4,4,5,5,5-nonafluoro-2-(trifluoromethyl)pent-2-ene was gradually occurring. After 4 days at 70° C. the isomerization was 90% complete. Next the reaction temperature was stepped to 100° C. and held for 3 hours with stirring to complete reaction, resulting in a final pressure of 272 psi. The reactor was then allowed to cool to room temperature overnight and residual pressure was vented. Once at atmospheric pressure, the reactor was disassembled and the reaction mixture was quenched with 200 mL water with stirring resulting in a two phase liquid mixture. The lower fluorochemical phase was recovered and washed with two 150 mL portions of water in a separatory funnel to remove residual ethylene carbonate and bromide catalyst. After the final water washing, 75.20 g of crude fluorochemical product was recovered. The crude product was analyzed by GC-FID revealing that it consisted of 89.5% desired product (2-fluoro-2-(1,1,2,2,2-pentafluoroethyl)-3,3-bis(trifluoromethyl)tetrahydrofuran). No unreacted 1,1,1,3,4,4,5,5,5 -nonafluoro-2-(trifluoromethyl)pent-2-ene or 1,1,1,2,3,4,5,5,5-nonafluoro-4-(trifluoromethyl)pent-2-ene was detected by GC. The identity of the desired product was verified by GC-MS analysis which indicated a mass of 344 amu and by $^{19}F$ NMR spectroscopy.

Example 2: 2-fluoro-3-(1,1,2,2,3,3,3-heptafluoropropyl)-2-[1,2,2,2-tetrafluoro-1-(trifluoromethyl)ethyl]-3-(trifluoromethyl)tetrahydrofuran 1,1,1,2,3,5,5,6,6,7,7,7-dodecafluoro-2,4-bis(trifluoromethyl)hept-3-ene (200.3 g, 445.04 mmol), triethylamine (49.5 g, 489.18 mmol), 2-bromoethanol (55.3 g, 442.53 mmol), diethylene glycol diethyl ether (300 g, 2235.90 mmol) and cesium fluoride (88.1 g, 579.96 mmol) in a 600 ml Parr pressure reactor. The mixture was heated to 75° C. for two days. The reaction mixture was then analyzed by GC-FID which indicated the reaction conversion of at least 42% to the product. The reaction mixture was washed with DI water four times, a total of 175 g product was collected which was dried over molecular sieves and then filtered. The product was fractionally distilled (b.p.~220° C.). The product structure, as shown in Table 1, was confirmed by GC-MS and $^1H$, $^{19}F$ NMR.

Example 3: 2-fluoro-5-methyl-2-(1,1,2,2,2-pentafluoroethyl)-3,3-bis(trifluoromethyl)tetrahydrofuran To a 600 mL Hastelloy Parr reactor were charged acetonitrile (53.6 g, 1310 mmol), tetrabutylammoniumbromide (40.9 g, 127 mmol), perfluoro-2-methyl-pentene (294 g, 979 mmol), and propylene oxide (59.4 g, 1020 mmol). The reactor was sealed, back filled with nitrogen, and vented 3 times to remove oxygen. The reactor was then heated to 70° C. At this temperature the reactor pressure was 30 psig. The temperature was increased to the final temperature of 100° C. and the pressure increased to 50 psig. The reaction was left to stir overnight and upon returning the reactor pressure was 20 psig. The reactor was cooled to 10° C. and a neat sample taken and analyzed by GC-FID showed an uncorrected 50% compound purity. Analysis by GC-MS of the neat sample confirmed the mass of the desired product as 358 amu with a purity of 53%. The reactor was then drained into a separatory funnel and washed twice with water (200 mL). The recovered material was placed on molecular sieves to remove water for distillation. The dried crude material was then transferred into a 500 mL distillation flask. The materials having low boiling point were distilled off at ambient pressure using a 15 tray Oldershaw vacuum jacketed distillation column set-up until the material coming over head had a boiling point of 125° C. The distillation flask was then cooled to room temperature and the remaining material was distilled under vacuum affording 222 grams of title compound as a clear colorless liquid which was analyzed by GC-FID indicating an uncorrected purity of 98.2%. Analysis of the isolated material by GC-MS and $^1H$, $^{19}F$ NMR confirmed the identity of the compound with a mass of 358 amu and an NMR purity of 96.4% 2-fluoro-5-methyl-2-(1,1,2,2,2-pentafluoroethyl)-3,3-bis(trifluoromethyl)tetrahydrofuran. The pour point of the isolated propylene oxide adduct (2-fluoro-5-methyl-2-(1,1,2,2,2-pentafluoroethyl)-3,3-bis(trifluoromethyl)tetrahydrofuran) was found to be surprisingly low (−85° C.) compared to the related ethylene oxide adduct of Example 1 (−11° C.), suggesting particular utility of 2-fluoro-5-methyl-2-(1,1,2,2,2-pentafluoroethyl)-3,3-bis(trifluoromethyl)tetrahydrofuran (Example 3) as a heat transfer fluid in applications that require low temperature performance.

Example 4: 2-fluoro-3-(1,1,2,2,3,3,3-heptafluoropropyl)-5-methyl-2-[1,2,2,2-tetrafluoro-1-(trifluoromethyl)ethyl]-3- (trifluoromethyl)tetrahydrofuran To a 300 mL Hasteloy Parr reactor was charged 1,1,1,2,3,5,5,6,6,7,7,7-dodecafluoro-2,4-bis(trifluoromethyl)hept-3-ene (98.7 g, 219 mmol), propylene oxide (14.0 g, 241 mmol), acetonitrile (15.31 g, 372.9 mmol), and tetrabutylammoniumbromide (11.06 g, 34.31 mmol). The reactor was sealed, back filled with nitrogen and vented 3 times to remove oxygen. The reactor was then heated to 100° C. at which point the reactor pressure was 45 psig. After stirring for 16 hours the pressure decreased to 35 psig. The reactor was cooled to 20° C. and its contents were poured into a separatory funnel. The reaction mixture was 2 phases before the addition of water. The fluorochemical layer was collected and a neat sample analyzed by GC-FID showed an uncorrected purity of 62% 2-fluoro-3-(1,1,2,2,3,3,3-heptafluoropropyl)-5-methyl-2-[1,2,2,2-tetrafluoro-1-(trifluoromethyl)ethyl]-3-(trifluoromethyl)tetrahydrofuran. The top phase remaining in the separatory funnel was washed with water (50 mL) twice. Analysis of the resulting fluorochemical phase by GC-FID showed an uncorrected purity of 30% 2-fluoro-3-(1,1,2,2,3,3,3-heptafluoropropyl)-5-methyl-2-[1,2,2,2-tetrafluoro-1-(trifluoromethyl)ethyl]-3-(trifluoromethyl)tetrahydrofuran. The fluorochemical layer collected earlier was washed with water (50 mL) twice and combined with the previously washed top phase in a bottle. The combined crude material was dried over molecular sieves for 2 hours under magnetic stirring. The dried crude material was then transferred into a 250 mL distillation flask. The low boiling point materials were distilled off at ambient pressure using a simple distillation set-up until the material coming overhead had a boiling point of 100° C. The distillation flask was then cooled to room temperature and the remaining material was distilled under vacuum (80° C./20 torr) affording the title compound as a bright yellow liquid which was analyzed by GC-FID, indicating an uncorrected purity of 89% 2-fluoro-3-(1,1,2,2,3,3,3-heptafluoropropyl)-5-methyl-2-[1,2,2,2-tetrafluoro-1-(trifluoromethyl)ethyl]-3-(trifluoromethyl)tetrahydrofuran. Analysis of the isolated material by GC-MS and $^1$H, $^{19}$F NMR spectroscopy confirmed the identity of the title compound with a mass of 508 amu and an NMR purity of 87% 2-fluoro-3-(1,1,2,2,3,3,3-heptafluoropropyl)-5-methyl-2-[1,2,2,2-tetrafluoro-1-(trifluoromethyl)ethyl]-3-(trifluoromethyl)tetrahydrofuran.

Example 5: 5-methyl-2,2,3,3-tetrakis(trifluoromethyl)tetrahydrofuran

To a 100 mL Parr reactor was charged 1,1,1,4,4,4-hexafluoro-2,3-bis(trifluoromethyl)but-2-ene (17 g, 56.659 mmol), tetrabutylammonium bromide (1.9 g, 5.9 mmol), propylene oxide (3.1 g, 53 mmol), and acetonitrile (21.3 g, 519 mmol). The reactor was sealed, then filled and vented with nitrogen 3 times, and finally backfilled with positive nitrogen pressure. The reactor was then heated to 100° C. overnight. At 100° C. the reactor pressure was 50 psig. In the morning the reactor pressure was 30 psig. The reactor was cooled, vented, and drained to a separatory funnel. The lower phase was collected and washed with equal volumes water 3 times. A sample was analyzed by GC and showed possible desired material at 90% purity. The sample was analyzed by GC-MS/FID and 1H/13C/19F-NMR techniques and was confirmed to be the desired product, 5-methyl-2,2,3,3-tetrakis(trifluoromethyl)tetrahydrofuran (16.2 grams at 87.7 absolute mass %.)

Test Methods

Boiling points were measured using ASTM D1120-94 "Standard Test Method for Boiling Point of Engine Coolants."

Pour points were determined by placing approximately 2 mL of the sample in a 4 mL glass vial into a manually temperature-controlled bath. Temperature was read with Analytical Instrument No. 325. Pour point is defined as the lowest temperature at which, after being tilted horizontally for 5 seconds, the sample is visually observed to flow.

Environmental lifetimes and Global Warming Potential (GWP) values were determined using methods described in Intergovernmental Panel on Climate Change (IPCC) Fifth Assessment Report (AR5) that consists of essentially three parts:

(1) Calculation of the radiative efficiency of the compound based upon a measured infrared cross-section for the compound.

(2) Calculation, measurement, or estimation of the atmospheric lifetime of the compound.

(3) Combination of the radiative efficiency and atmospheric lifetime of the compound relative to that of CO2 over a time horizon of 100 years.

The three steps used to calculate a GWP were as follows. A gas standard of the material to be assessed, having a known and documented concentration was prepared at the 3M Environmental Lab and used to obtain the FTIR spectra of this compound. Quantitative gas phase, single component FTIR library reference spectra were generated at two different concentration levels by diluting the sample standard with nitrogen using mass flow controllers. The flow rates were measured using certified BIOS DRYCAL flow meters (Mesa Labs, Butler, N.J., US) at the FTIR cell exhaust. The dilution procedure was also verified using a certified ethylene calibration gas cylinder. Using methods described in AR5, the FTIR data was used to calculate the radiative efficiency, which in turn was combined with the atmospheric lifetime to determine the global warming potential (GWP) value.

A Global Warming Potential (GWP) value was determined for Examples 1, 2, CE1, and CE2 using the three-part AR5 method. The atmospheric lifetime of each material was determined from relative rate studies utilizing chloromethane ($CH_3Cl$) as a reference compound. The pseudo-first order reaction rates of the reference compound and the test compound with hydroxyl radicals (.OH) was determined in a laboratory chamber system. The atmospheric lifetime of the reference compound is documented in the literature, and based on this value and the pseudo-first order rates measured in the chamber experiments, the atmospheric lifetime for each specimen was determined. The concentrations of gases in the test chamber were quantified by FTIR. The measured atmospheric lifetime value of each fluid was used for GWP calculation.

The 4-hour acute inhalation toxicity in rats (LC-50) was measured by dosing animals in air at the amounts shown in Table 2 for 4 hours, followed by 14-day post-dose monitoring. Based on the animal test results and the vapor concentration of the test compound, the LC-50 values were estimated.

The acute single dose oral toxicity of Comparative Example CE2 was examined in rats dosed at 2000 mg/kg body weight. No adverse clinical observations were noted during the post dose recovery period and necropsy results were normal for all animals. Based on this study, the LD50 of CE2 was estimated to be >2000 mg/kg body weight.

In these Examples, values of Log KOW (octanol/water partition coefficients) were determined by HPLC using the method described in OECD Method 117.

Results

The properties and environmental lifetime results are summarized in Table 2 and illustrate that the hydrofluoroethers of the present invention, Examples 1 and 2, have substantially higher boiling points and significantly shorter environmental lifetimes compared to hydrofluoroethers of similar molecular weight (CE1 and CE2). This is a surprising and unexpected result and makes these materials particularly useful as heat transfer fluids in apparatuses.

TABLE 2

Properties of Illustrative and Comparative HFEs

| Property | Example 1* | Example 2 | Comparative Example CE1 | Comparative Example CE2 |
|---|---|---|---|---|
| Molecular Weight, g/mol | 344.1 | 494.12 | 350 | 528 |
| Boiling Point, ° C. | 150.1 | 185 | 98 | 167 |
| Pour/Freeze Point, ° C. | −11 | −63 | −38 | −50 |
| Density at 25° C., g/mL | 1.7244 | 1.84 | 1.66 | 1.79 |
| Flash point, ° C. | none | none | none | none |
| Atmospheric Lifetime, yr | 0.37 | 0.1 | 3.8 | 5.6 |
| GWP, 100 yr | 17 | 11 | 200 | 436 |
| LC-50 (4 hr Inhalation rats) or LD50 | >1000 ppmv | N/A | >430 mg/L | LD50 >2000 mg/kg |
| Log KOW | 4.4 | 5.8 | 4.3 | 6.6 |

*Prepared via Synthesis Procedure A

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows. All references cited in this disclosure are herein incorporated by reference in their entirety.

What is claimed is:

1. A compound represented by the following general formula (I):

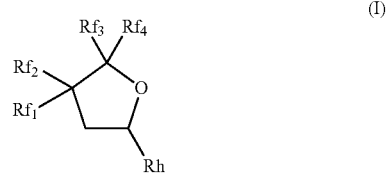

wherein each of $Rf_1$ and $Rf_2$ is, independently, F, $CF_3$, $C_2F_5$, $C_3F_7$, or $C_4F_9$, with the proviso that if either of $Rf_1$ and $Rf_2$ is fluorine, then the other is not fluorine;
$Rf_3$ is F, $CF_3$, $C_2F_5$, $C_3F_7$ or $CF(CF_3)_2$;
$Rf_4$ is F, $CF_3$, $C_2F_5$, $C_3F_7$ or $CF(CF_3)_2$; and
Rh is $CH_3$ or $C_2H_5$.

2. The compound of claim 1, wherein $Rf_1$ and $Rf_2$ are either both $CF_3$ or $Rf_1$ is $CF_3$ and $Rf_2$ is $C_2F_5$ or $C_3F_7$ or $C_4F_9$.

3. The compound of claim 1, wherein $Rf_3$ is $C_2F_5$ or $CF(CF_3)_2$.

4. The compound of claim 1, wherein Rh is $CH_3$.

5. A compound represented by the following general formula (I):

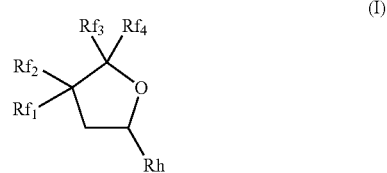

where $Rf_1$ is $CF_3$, $C_2F_5$ or $C_3F_7$;
$Rf_2$ is $C_2F_5$, $C_3F_7$, or $C_4F_9$;
$Rf_3$ is $CF(CF_3)_2$ or $C_3F_7$;
$Rf_4$ is F; and
Rh is H.

6. The compound of claim 5, wherein $Rf_1$ is $CF_3$ and $Rf_2$ is $C_2F_5$, $C_3F_7$ or $C_4F_9$.

7. A compound represented by the following general formula (I):

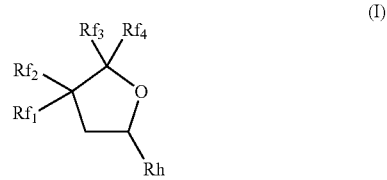

where one or two pairs of Rf groups from among $Rf_1$, $Rf_2$, $Rf_3$, and $Rf_4$ are linked together to form a 5 or 6 membered perfluorinated carbon ring; and
Rh is $CH_3$, $C_2H_5$ or H;
wherein any of $Rf_1$, $Rf_2$, $Rf_3$, and $Rf_4$ that are not linked together are as follows:
each of $Rf_1$ and $Rf_2$ is, independently, F, $CF_3$, $C_2F_5$, $C_3F_7$, or $C_4F_9$ with the proviso that if either of $Rf_1$ and $Rf_2$ is fluorine, then the other is not fluorine;

$Rf_3$ is F, $CF_3$, $C_2F_5$, $C_3F_7$ or $CF(CF_3)_2$; and $Rf_4$ is F, $CF_3$, $C_2F_5$, $C_3F_7$ or $CF(CF_3)_2$.

8. A working fluid comprising at least one compound of claim 1, claim 5, or claim 7, wherein the compound is present in the working fluid at an amount of at least 25% by weight based on the total weight of the working fluid.

9. An apparatus for heat transfer comprising:

a device; and a mechanism for transferring heat to or from the device, the mechanism comprising a working fluid that comprises a compound represented by the following general formula (I):

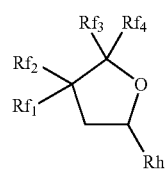

(I)

where each of $Rf_1$ and $Rf_2$ is, independently, F, $CF_3$, $C_2F_5$, $C_3F_7$, or $C_4F_9$ with the proviso that if either of $Rf_1$ and $Rf_2$ is fluorine, then the other is not fluorine;

$Rf_3$ is F, $CF_3$, $C_2F_5$, $C_3F_7$ or $CF(CF_3)_2$;

$Rf_4$ is F, $CF_3$, $C_2F_5$, $C_3F_7$ or $CF(CF_3)_2$; and

Rh is $CH_3$, $C_2H_5$, or H.

10. The apparatus for heat transfer of claim 9, wherein $Rf_1$ and $Rf_2$ are either both $CF_3$ or $Rf_1$ is $CF_3$ and $Rf_2$ is $C_2F_5$ or $C_3F_7$ or $C_4F_9$.

11. The apparatus for heat transfer of claim 9, wherein $Rf_3$ is $C_2F_5$ or $CF(CF_3)_2$.

12. The apparatus for heat transfer of claim 9, wherein Rh is H or $CH_3$.

13. The apparatus for heat transfer of claim 9, wherein the compound comprises the compound of claim 1.

14. The apparatus for heat transfer of claim 9, wherein the device is selected from a microprocessor, a semiconductor wafer used to manufacture a semiconductor device, a power control semiconductor, an electrochemical cell, a battery pack, an electrical distribution switch gear, a power transformer, a circuit board, a multi-chip module, a packaged or unpackaged semiconductor device, a fuel cell, and a laser.

15. The apparatus for heat transfer of claim 9, wherein the mechanism for transferring heat is a component in a system for maintaining a temperature or temperature range of an electronic device.

16. A method of transferring heat comprising:

providing a device; and transferring heat to or from the device using a heat transfer fluid that comprises a compound represented by the following general formula (I):

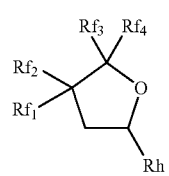

(I)

where each of $Rf_1$ and $Rf_2$ is, independently, F, $CF_3$, $C_2F_5$, $C_3F_7$, or $C_4F_9$ with the proviso that if either of $Rf_1$ and $Rf_2$ is fluorine, then the other is not fluorine;

$Rf_3$ is F, $CF_3$, $C_2F_5$, $C_3F_7$ or $CF(CF_3)_2$;

$Rf_4$ is F, $CF_3$, $C_2F_5$, $C_3F_7$ or $CF(CF_3)_2$; and

Rh is $CH_3$, $C_2H_5$, or H.

17. A process for making a compound having the following general formula (I):

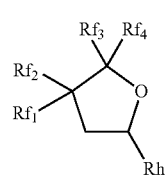

(I)

where each of $Rf_1$ and $Rf_2$ is, independently, F, $CF_3$, $C_2F_5$, $C_3F_7$, or $C_4F_9$ with the proviso that if either of $Rf_1$ and $Rf_2$ is fluorine, then the other is not fluorine;

$Rf_3$ is F, $CF_3$, $C_2F_5$, $C_3F_7$ or $CF(CF_3)_2$;

$Rf_4$ is F, $CF_3$, $C_2F_5$, $C_3F_7$ or $CF(CF_3)_2$; and

Rh is $CH_3$, $C_2H_5$, or H, the process comprising the step of reacting a perfluorinated olefin having the following general structure (II)

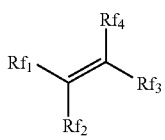

(II)

where each of $Rf_1$ and $Rf_2$ is, independently, F, $CF_3$, $C_2F_5$, $C_3F_7$, or $C_4F_9$, with the proviso that if either of $Rf_1$ and $Rf_2$ is F, then the other is not fluorine; and $Rf_3$ is F, $CF_3$, $C_2F_5$, $C_3F_7$, or $CF(CF_3)_2$; and $Rf_4$ is F, $CF_3$, $C_2F_5$, $C_3F_7$ or $CF(CF_3)_2$;

with a cyclic organic carbonate or an organic epoxide in the presence of a catalyst.

18. The process of claim 17, wherein the cyclic organic carbonate comprises ethylene carbonate or propylene carbonate.

19. The process of claim 18, wherein the organic epoxide comprises ethylene oxide or propylene oxide.

20. The process of claim 18, wherein the catalyst is a halide salt.

21. The process of claim 18, wherein the perfluorinated olefin of general structure (II) is generated in-situ from an isomeric perfluorinated olefin via catalytic isomerization.

* * * * *